(12) United States Patent
Caton et al.

(10) Patent No.: US 11,491,309 B2
(45) Date of Patent: Nov. 8, 2022

(54) DELIVERY GUIDEWIRE

(71) Applicant: Cephea Valve Technologies, Inc., Santa Clara, CA (US)

(72) Inventors: Curtis James Caton, San Jose, CA (US); Randolf von Oepen, Aptos, CA (US); Juan F. Granada, Saddle River, NJ (US)

(73) Assignee: Cephea Valve Technologies, Inc., Santa Clara, CA (US)

( * ) Notice: Subject to any disclaimer, the term of this patent is extended or adjusted under 35 U.S.C. 154(b) by 365 days.

(21) Appl. No.: 16/683,500

(22) Filed: Nov. 14, 2019

(65) Prior Publication Data

US 2020/0155803 A1 May 21, 2020

Related U.S. Application Data

(60) Provisional application No. 62/769,040, filed on Nov. 19, 2018.

(51) Int. Cl.
*A61M 25/01* (2006.01)
*A61M 25/09* (2006.01)

(52) U.S. Cl.
CPC ............... *A61M 25/0113* (2013.01); *A61M 2025/09083* (2013.01); *A61M 2025/09133* (2013.01); *A61M 2025/09166* (2013.01); *A61M 2025/09175* (2013.01); *A61M 2210/125* (2013.01)

(58) Field of Classification Search
CPC ........ A61M 25/09; A61M 2025/09083; A61M 2025/09133; A61M 2025/09166; A61M 2025/09175; A61M 2025/09091; A61M 2210/125
See application file for complete search history.

(56) References Cited

U.S. PATENT DOCUMENTS

| | | | |
|---|---|---|---|
| 7,715,903 B2 * | 5/2010 | Hartley | A61M 25/09033 600/585 |
| 9,072,872 B2 * | 7/2015 | Asleson | A61B 18/1492 |
| 10,368,911 B2 * | 8/2019 | Davies | A61B 90/39 |
| 2004/0167439 A1 * | 8/2004 | Sharrow | A61M 25/09 600/585 |
| 2012/0016342 A1 | 1/2012 | Brecker | |
| 2017/0266434 A1 | 9/2017 | Daniels et al. | |
| 2018/0311477 A1 * | 11/2018 | Telang | A61M 25/09 |
| 2019/0167305 A1 * | 6/2019 | Pedersen | A61B 17/3468 |

FOREIGN PATENT DOCUMENTS

| EP | 0363661 | 4/1990 |
|---|---|---|
| EP | 3395393 | 10/2018 |
| WO | WO 2015019132 | 2/2015 |

* cited by examiner

*Primary Examiner* — Devin B Henson
(74) *Attorney, Agent, or Firm* — Workman Nydegger (57) ABSTRACT

A delivery guidewire for navigating a catheter in the heart to deliver a valve prosthesis. The delivery guidewire comprising an elongated core, an outer sleeve disposed on the elongated core, and a coil disposed on a distal portion of the elongated core. The delivery guidewire having a first section having a generally uniform diameter and a second section having a tapering section. A distal portion of the second section of the delivery guidewire comprises a pigtail shape atraumatic tip which can remain in the left ventricle.

20 Claims, 5 Drawing Sheets

DELIVERY GUIDEWIRE

CROSS-REFERENCE TO RELATED APPLICATIONS

This application claims priority to U.S. Provisional Patent Application No. 62/769,040, filed Nov. 19, 2018, the entire contents of which are incorporated by reference herein.

BACKGROUND OF THE INVENTION

1. The Field of the Invention

The present invention generally relates to a guidewire useable for various medical procedures.

2. The Relevant Technology

During certain medical procedures, placement of a medical device mounted within a delivery catheter involves advancing the delivery catheter and medical device through the tortuous anatomy of a patient. Typically, to aid with positioning of the medical device, such as a delivery catheter, a clinician advances a guidewire to a target location through the vasculature and then advances the catheter along the guidewire to the target location using a rapid exchange or over-the-wire technique. The guidewire keeps the catheter from getting caught in, or interfering with other anatomical structures.

Steerable systems are often used to position a catheter in the heart, which typically requires navigating a number of valves, and in some cases, the arteries as well. Steerable systems, even systems with a high degree of steerability, may still rely on a guidewire due to the power of deflection forces in the heart which can force the tip of the device into the wall of the heart and cause significant damage.

Guidewires are used in heart valve replacement or repair procedures to provide a stable track for a delivery catheter to deliver a valve prosthesis. Guidewires used in these procedures have a degree of steerability and rigidity, and in some cases must be able to puncture the septum in order to move through different chambers of the heart. For this reason, stainless steel guidewires are typically used for such applications.

However, there are a number of problems and risks associated with stainless steel guidewires or guidewires made from similar materials. Stainless steel guidewires are particularly susceptible to kinking or deforming as a result of deflection forces. For example, this may occur when a catheter containing a guidewire is deflected, causing the coincident portion of the guidewire to plastically deform. Additionally, the bending radii in the heart relative to the size of the device are very small. These tight deflections may plastically deform any guidewire having a stainless steel core. Though it is possible to avoid plastic deformation of a guidewire by pulling the guidewire back into the catheter, this is not a safe long-term solution. If the guidewire pulled back into the catheter is forgotten about and is deformed or becomes deformed, the plastically deformed guidewire will be locked into the system. Once this happens, the catheter will have to be replaced before the procedure can continue. Before replacing the delivery catheter, a new guidewire will have to be placed, which in turn prolongs the time needed to complete the procedure.

One technique commonly used with guidewires for transcatheter mitral valve replacements is to place the guidewire through the septum and through the mitral valve, then out the aortic valve into the aorta, and sometimes even up into the carotid arteries. This technique provides a predetermined track for the delivery catheter to follow through the septum and into the mitral valve. However, this technique poses serious health risks for patients. When the guidewire is passed through the aortic valve from the ventricle side, there is a risk of the guidewire catching on a diseased valve and potentially causing more damage. Similarly, bending the guidewire in a full 360° or more bend inside the heart puts a significant amount of pressure on the heart walls and on a potentially diseased aortic valve, and poses the additional risk of perforation in patients with diseased aortic or carotid arteries. Also, the guidewire can cause plaque to become dislodged from whichever locations the guidewire must pass through, thereby increasing the risk of stroke.

Accordingly, there are a number of problems in the prior art that need to be addressed in the field of guidewires, particularly for those designed for and intended for use in cardiac valve replacement and/or repair applications.

BRIEF SUMMARY OF THE INVENTION

The present invention is directed to a guidewire for passage through a patient's vasculature to a target location and is particularly suitable for use in cardiac procedures.

In a first embodiment, a delivery guidewire may comprise an elongated core having a proximal end, a distal end, and a length extending therebetween and defining a longitudinal axis. The delivery guidewire may also have a coil disposed on the elongated core. The distal end of the delivery guidewire may have an atraumatic tip. The elongated core may have a first section having a generally uniform diameter and a second section having a diameter that tapers towards the distal end. The atraumatic tip may comprise a pigtail shape comprising a distal portion of the distal end of the elongated core of the delivery guidewire. The elongated core may be made from a superelastic material, such as nitinol. The guidewire may optionally have an outer sleeve disposed on or covering the elongated core and/or the coil.

In another embodiment, a delivery guidewire may comprise an elongated core having a proximal end, a distal end, and a longitudinal axis therebetween. The elongated core may comprise a first section of generally uniform diameter and a second section comprising a tapering section. The first section may be proximal to the second section and the first section may be defined from the second section at a tapering point. An outer sleeve may be disposed on the elongated core and may extend along the longitudinal axis. A coil may be disposed on the elongated core. The distal end of the elongated core may include an atraumatic tip. The atraumatic tip may comprise a distal portion of the second section of the elongated core, and the distal portion may form a pigtail shape.

In another embodiment, a delivery guidewire may comprise an elongated core having a proximal end, a distal end, and a longitudinal axis therebetween. The elongated core may comprise a first section of generally uniform diameter and a second section comprising a tapering section. The first section may be proximal to the second section and the first section may be defined from the second section at a tapering point. An outer sleeve may be disposed on the elongated core and may extend along the longitudinal axis. The distal end of the elongated core may include an atraumatic tip. The atraumatic tip may comprise a distal portion of the second section of the elongated core, and the distal portion may form a pigtail shape. A coil may be disposed on the distal portion of the second section and may extend along a portion of the pigtail shape. The delivery guidewire may further comprise a substantially straight length proximal to the start of the pigtail shape, and a secondary bend in the elongated core proximal to the straight length.

These and other objects and features of the present invention will become more fully apparent from the following description and appended claims or may be learned by the practice of the invention as set forth hereinafter.

BRIEF DESCRIPTION OF THE DRAWINGS

In order to describe the manner in which at least some of the advantages and features of the invention may be obtained, a more particular description of embodiments of the invention will be rendered by reference to specific embodiments thereof which are illustrated in the appended drawings. Understanding that these drawings depict only typical embodiments of the invention and are not therefore to be considered to be limiting of its scope, embodiments of the invention will be described and explained with additional specificity and detail through the use of the accompanying drawings in which.

DETAILED DESCRIPTION OF THE PREFERRED EMBODIMENTS

Mitral valve repair or replacement procedures typically require a transseptal approach in which a catheter configured to deliver a mitral valve prosthesis or other interventional device to the annulus of the human mitral valve must pass through the septum, from the right to left atrium, of the heart. Though some delivery catheters are steerable, it is preferable to use a guidewire to ensure that the delivery catheter remains on track and does not cause damage to surrounding tissue during the delivery process. Guidewires keep delivery catheters from getting caught or interfering with mitral valve anatomy or other surrounding anatomy. In some cases, to ensure free passage through the mitral annulus, a balloon catheter, typically used to expand the puncture size at the septum, may be inflated in the right atrium. The inflated balloon may be run over the guidewire and through the mitral annulus.

Traditional guidewires are generally made from stainless steel which tend to kink when navigating the small deflection radii of the right atrium to point toward the mitral valve. These tight deflections may plastically deform a guidewire having a stainless steel core or that are otherwise formed from a material with similar plastic/elastic properties. In cases where this occurs, the guidewire must be pulled back into the catheter and repositioned. If the guidewire has been plastically deformed, pulling the guidewire back into the catheter can risk the guidewire becoming locked into the catheter, thereby requiring that the catheter and guidewire be replaced before the procedure can continue.

In order to guide a delivery system through the mitral annulus, a support is typically needed, even when a catheter may be steerable by deflecting the distal portion in different planes. One technique is to place the guidewire through the septum, then through the mitral valve, then out the aortic valve and into the aorta, and in some cases into the carotid artery. This technique provides adequate support to allow the delivery catheter to travel through the septum and into the mitral valve. However, it does pose a serious health risk to patients. For example, passing the guidewire through the aortic valve from the ventricle side risks the guidewire catching on a potentially diseased valve causing damage, and subsequently increasing the risk of perforation in patients with diseased arteries. Similarly, bending the guidewire in a full 360° or more bend inside the heart puts a substantial amount of pressure on the walls of the heart and on a potentially diseased aortic valve. Extensive navigation of a guidewire can dislodge plaque from any of the locations it has to pass through, resulting in an increased risk of stroke. Due to these risks it is generally safer to leave the guidewire in the left ventricle.

During valve replacement or repair procedures, it may be preferred for the tip of the guidewire to be placed in the left ventricle in order to allow the delivery catheter to track directly into the mitral valve. Traditional guidewire shapes, such as straight, angled, or J-tip, are not atraumatic enough to be placed in the left ventricle without significant risk of perforating a diseased heart wall. Pigtail-shaped guidewires provide an atraumatic tip for these procedures. However, the coil shape generally requires a stainless steel core, rendering them susceptible to kinking, which as described above, results in higher procedural risk to the patient. Until now, there has not been a guidewire capable of being placed in the left ventricle without substantial risk of kinking or causing further damage to the patient's heart.

The guidewire of the present invention can be used during a transseptal procedure, such as a procedure to replace or repair a heart valve. During a transseptal procedure a guidewire aids with placement of a transseptal catheter that can be used to deliver a valve prosthesis and/or other interventional device(s) to the annulus of the human mitral valve, aortic valve, or other targeted cardiac valve, or provide access to implant a fastener or other structure to repair the mitral valve, aortic valve, or other targeted cardiac valve.

Figure 1:
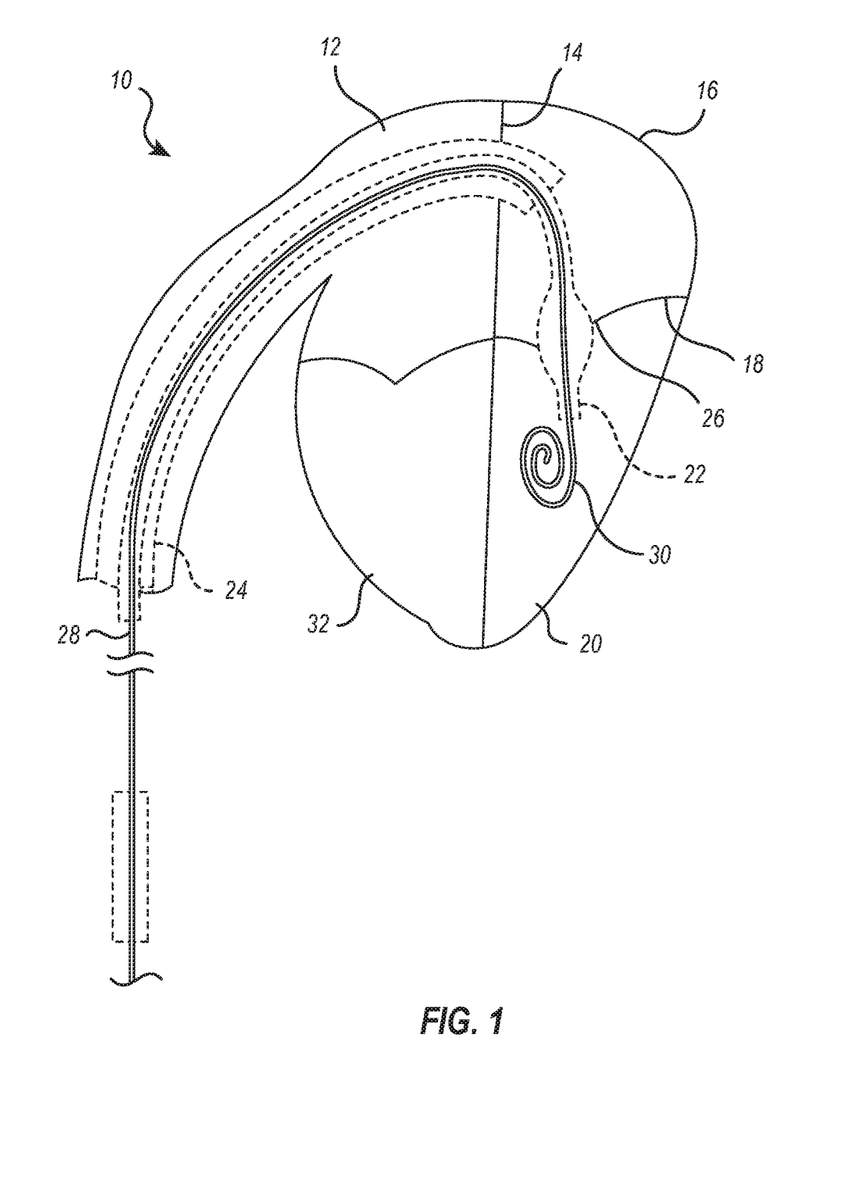
FIG. 1 discloses aspects of a schematic representation of transseptal procedure performed on a human heart.

FIG. 1 illustrates a trans-septal approach 10, in which a first guidewire is inserted into the right atrium 12 and punctures the septum 14, known as a septal crossing, which is performed by puncturing the septum 14 using a puncturing device, such as a needle, a special guidewire, septum crossing device, or other device capable of puncturing the septum 14. After crossing the septum 14 to enter the left atrium 16, the first guidewire used to access and cross the septum 14 is advanced, or can be exchanged for a second guidewire that can be advanced, through the mitral valve 18, and into the left ventricle 20. In some cases, this may be done with the aid of another catheter, such as a steering catheter.

Once the guidewire (e.g., second guidewire) is in place, a balloon 22 may be used to ensure that when the delivery catheter 24 for delivery of a valve prosthesis is inserted, it will not interfere with parts of the mitral annulus 26. A balloon 22 can be pushed over the second guidewire to ensure clear passage through the annulus 26 and confirm that neither the second guidewire or the delivery catheter 24 will become entangled in chordae or passed behind a papillary muscle. For example, the balloon 22 can be inflated to expand the mitral annulus 26, then deflated and advanced into the left ventricle 20, and re-inflated and drawn back through the mitral annulus 26. If an undesired interaction is discovered, the procedure can be repeated to further expand the mitral annulus 26.

After use of a balloon 22 confirms that there is no interference with any parts of the mitral annulus 26, a guidewire exchange catheter can be placed over the second guidewire and the distal tip of a guidewire exchange catheter can be positioned distally of the mitral annulus 26. When in place, the second guidewire is removed and the guidewire 28 of the present invention can be advanced into the left ventricle 20. Thereafter, the guidewire exchange catheter can be removed and a desired procedure performed, such as repair or replacement of the mitral valve.

After positioning the guidewire 28 and confirming that the guidewire does not interfere with the mitral annulus 26 or associated mitral apparatus, the delivery catheter 24 may be introduced. The guidewire 28 may prevent the delivery catheter 24 from catching or interfering with the tissue associated with the mitral valve 18, such as the papillary muscles or chordae connected to the leaflets of the mitral valve 18. Additionally, the soft coiled tip or pigtail shape tip 30 of the guidewire 28 may remain in the left ventricle 20 without causing any damage during the mitral valve repair or replacement procedure, thereby eliminating the need to advance the guidewire 28 beyond the left ventricle 20 such as into the aortic valve.

Figure 2:
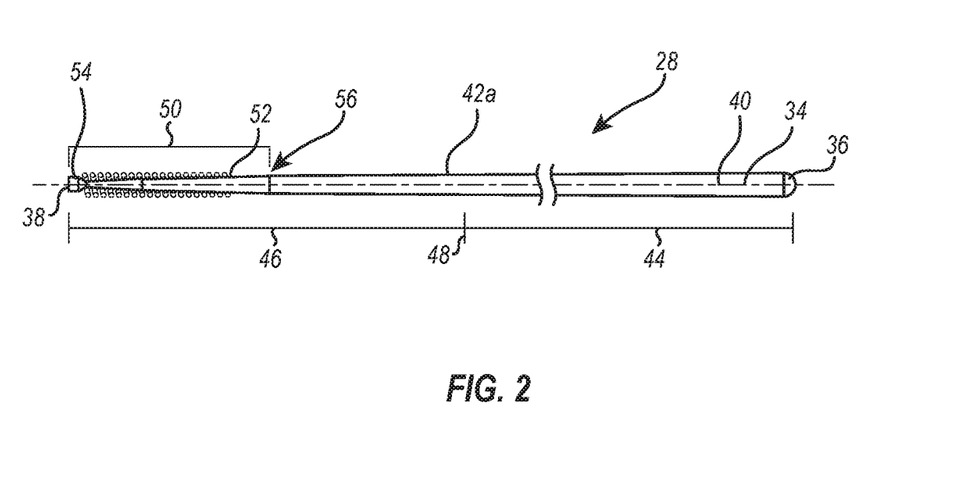
FIG. 2 discloses aspects of an example guidewire of the present disclosure.

FIG. 2 illustrates an embodiment of the guidewire 28 extended in a straight configuration. The guidewire 28 may comprise an elongated core 40 having a proximal end 36 and a distal end 38 with a length extending along a longitudinal axis 34. The elongated core 40 may be surrounded by a covering layer, which may comprise an outer sleeve 42a. A first section 44 of the guidewire 28 may be located closest to the proximal end 36 and may include the proximal end 36 and have a uniform diameter. A second section 46 of the guidewire 28 may be closest to the distal end 38 and may include the distal end 38. The second section 46 may have a tapered profile or progressive diameter along the length of the second section 46. The second section 46 may be distinguished from the first section 44 at a tapering point 48 on the elongated core 40 of the guidewire 28 where the diameter of the elongated core 40 begins to taper or decrease towards the distal end 38. A distal portion 50 of the second section 46 of the guidewire 28 may include a coil 52 coupled to the elongated core 40, and the distal end 38 of the guidewire 28 may comprise an atraumatic tip 54.

The elongated core 40 may be formed of a superelastic material, such as nitinol. Nitinol, and/or some other superelastic material, may avoid plastic deformation that would occur with a guidewire core formed from traditional materials such as stainless steel. With a limited amount of space in the right atrium 12 for movement and deflection of the guidewire 28, superelastic materials may advantageously increase the deflection capabilities of the guidewire 28. The elongated core 40 formed of superelastic material may impart the guidewire 28 with a sufficient degree of flexibility to avoid kinking or plastic deformation, thereby avoiding the risk of locking a kinked or plastically deformed guidewire within a catheter. An elongated core 40 containing superelastic material may be enabled to deflect through radii of about 5 mm to about 20 mm, about 8 mm to about 17 mm, about 10 mm to about 15 mm, about 12 mm to 14 mm.

Generally, the guidewire 28 may have a length of at least twice the length of a delivery catheter 24 intended for use in the procedure. In some embodiments, the guidewire 28 may have a length of at least 200 cm to 450 cm, about 250 cm to 400 cm, about 275 cm to 375 cm, or about 300 cm to 365 cm. An assembled guidewire 28, or a guidewire including a covering layer, may have a maximum outside diameter of about 0.025" to 0.037", 0.027" to 0.036", 0.028" to 0.036", or 0.029" to 0.036". The covering layer may include at least one or more of an outer sleeve 42a or a coil 52 covering the elongated core 40. In some embodiments, a coil 52 may be applied to the elongated core 40 under or over an outer sleeve 42a disposed on at least a portion the elongated core 40. The elongated core 40 may have a maximum outside diameter of about 0.025" to 0.034", 0.026" to 0.033", 0.027" to 0.033", 0.028" to 0.032", 0.030" to 0.032", or 0.029" to 0.031". It will be understood that the length and diameters can be larger or smaller than those expressly identified herein. As an example, the diameter of the guidewire can be the same as commonly available guidewires like 0.010", 0.014", 0.018", 0.021" 0.028," 0.035", and all other increments in-between.

In some embodiments, an outer sleeve 42a may impart the elongated core 40, with a substantial degree of lubricity and low surface friction to allow the guidewire 28 to easily slide within the delivery catheter 24. In some embodiments, the entire length of the guidewire 28, including the section having a coil 52, may be covered by an outer sleeve 42a. In another embodiment, the outer sleeve 42a may cover the length of the elongated core 40 up to a section of the elongated core 40 having a coil 52. In one configuration, the outer sleeve 42a is a polymeric sleeve or jacket. In some embodiments, the polymeric sleeve further comprises polytetrafluoroethylene (PTFE) shrink tubing.

Figure 3:
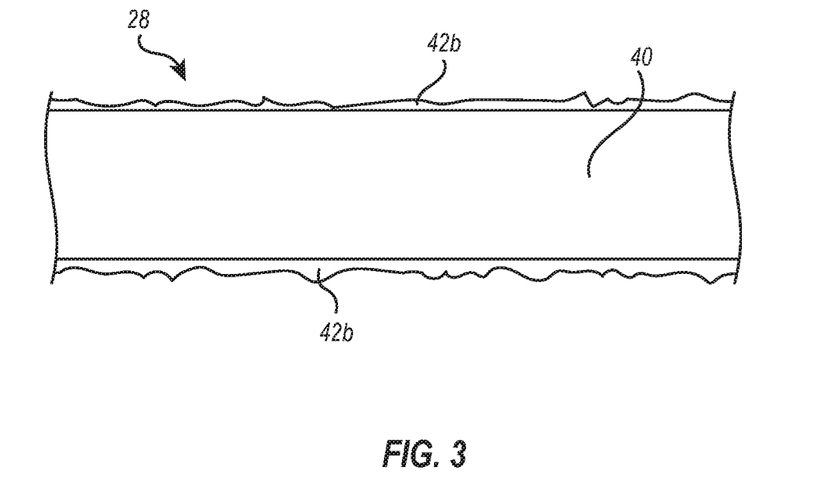
FIG. 3 discloses aspects of a cross-sectional side view of another guidewire according to one embodiment of the present disclosure.

The outer sleeve 42a, depicted in FIG. 2, may have a smooth surface resulting in very low surface friction, which makes is very easy to move the guidewire 28 back and forth in a catheter, for example, a guidewire exchange catheter or a delivery catheter 24. Also, the outer sleeve 42a may protect transitional zones 56 along the length of the guidewire 28 from becoming caught in a catheter or in the anatomy of the patient. Transitional zones 56 include areas along the length of the guidewire 28 having differing structural elements, for example, the outer sleeve 42a may help to seal and smooth the transition between the elongated core 40 and the portion of the guidewire core covered by the coil 52. Additionally, in certain configurations, the outer sleeve 42b can non-uniformly shrink or be formed on the elongated core 40 and/or coil 52 to create a textured surface 42b with numerous peaks and troughs, as illustrated in FIG. 3. The textured surface 42b can be have a uniform or non-uniformed texture. In either case, the textured surface 42b may reduce frictional contact between the guidewire 28 and the delivery catheter 24, thereby improving relative movement between the guidewire 28 and the delivery catheter 24. The different shrink ratio may be achieved by different coloring pigments, such as by applying stripes, lines, or other geometric patterns.

While reference to the outer sleeve 42a,42b being a PTFE shrink tubing, it will be understood that the outer sleeve 42a,42b can include polyolefin, polyvinyl chloride (PVC), fluoroelastomers such as Viton®, chloroprene polymers such as Neoprene®, polytetrafluoroethylene (PTFE), fluorinated ethylene propylene (FEP), and polyvinylidene fluoride (FVDF) polymers such as Kynar®.

Figure 4:
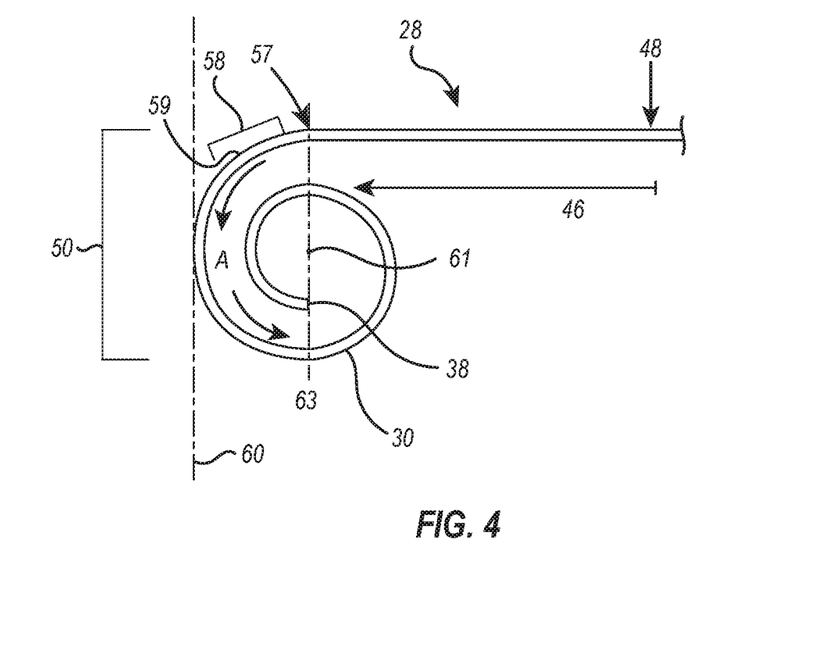
FIG. 4 discloses aspects of an expanded view of a second section of a guidewire of the present disclosure having a pigtail shape.

Returning now to FIG. 2, the elongated core 40, may have a first section 44 having a generally uniform diameter and a second section 46 that is tapered. The second section 46 may begin at a tapering point 48 proximal to the distal end 38 of the guidewire 28. The taper of the second end 46 may cause the core of the guidewire 28 to decrease in outside diameter towards the distal end 38. In some embodiments, the tapering point 48 may be located on the guidewire 28 at a specific distance from the start of a pigtail 30 shape comprising a portion 50 of the second section, as also shown in FIG. 4. The tapering point 48 may be located 0 cm to 10 cm proximal to the start 57 of the pigtail shape 30, or 2 cm to 9 cm proximal to the start 57 of the pigtail shape 30, or 3 cm to 8 cm proximal to the start 57 of the pigtail shape 30, or 4 cm to 7 cm proximal to the start 57 of the pigtail shape 30, or 5 cm to 6 cm proximal to the start 57 of the pigtail shape 30. Dimensions within the foregoing ranges have been found to be effective in cardiac interventional procedures, particularly for guiding a delivery catheter or other catheter device in a mitral valve repair or replacement procedure.

The second section 46 of the guidewire 28 may comprise at least 10 cm to 30 cm of the total length of the guidewire 28, or 11 cm to 28 cm of the total length of the guidewire 28, or 12 cm to 26 cm of the total length of the guidewire 28, or 14 cm to 24 cm of the total length of the guidewire 28. Dimensions within the foregoing ranges have been found to be effective in cardiac interventional procedures, particularly for guiding a delivery catheter or other catheter device in a mitral valve repair or replacement procedure.

Turning now to FIG. 4, a coil 52 may be applied to a portion 50 of the second section 46 of the guidewire 28. The coil may be a radiopaque coil. The coil 52 may comprise metals with a high atomic mass to be better visible under X-ray. For example, the coil 52 may be fabricated from platinum, platinum iridium, gold, silver, tantalum, etcetera. The coil 52 may cover a portion 50 of the second section 46 closest to the distal end 38 of the guidewire 28. The coil 52 may increase the bending stiffness of the guidewire 28. The increase in bending stiffness may also create a weak point or "kink point" in the guidewire 28 where it may form a tight bend when force is applied. This tight bend may pose an increased risk of perforating the heart wall if this tight bend is inadvertently pushed into the wall. Therefore, the coil 52 starting point 59 may be positioned so that the guidewire 28 is less prone to developing a weak point. For example, in one embodiment, the coil 52 may be attached to the guidewire 28 beginning at a first curved section 58 of the pigtail shape 30 and continuing towards the distal end 38. By starting the coil 52 at or within a first curved section 58, the potential weak point is contained within the pigtail shape 30, thereby lowering the risk of the guidewire 28 forming a tight bend or weak point capable of kinking and damaging surrounding tissue 60. For example, the coil 52 may start at a location about 1 cm to about 4 cm distal of the start 57 of the pigtail shape.

Figure 5:
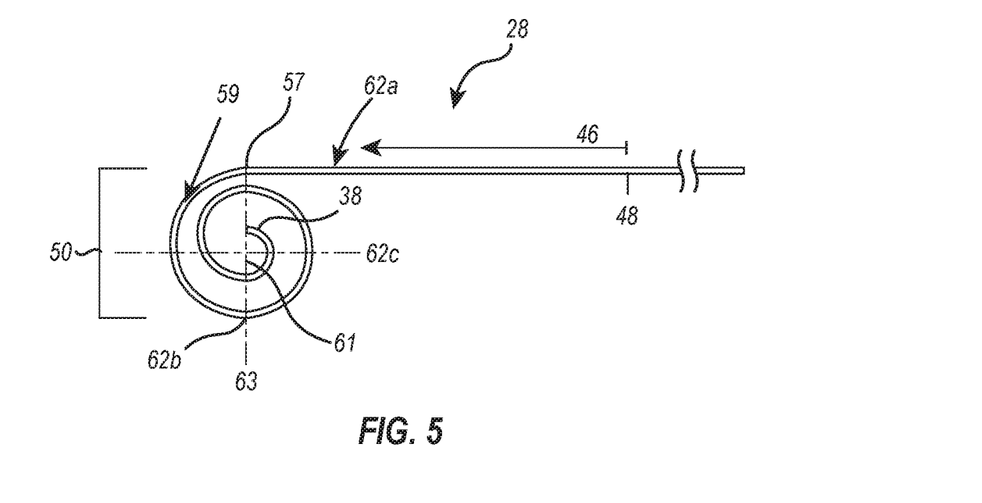
FIG. 5 discloses aspects of an expanded view of a second section of a guidewire of the present disclosure having a pigtail shape.

In another embodiment, illustrated in FIG. 5, the coil 52 (as shown in FIG. 2) may begin at various alternative coil starting points 62A, 62B, 62C on the guidewire 28. In one embodiment, the coil 52 may begin at an alternative coil starting point 62A on the guidewire 28 that is proximal to the start 57 of the pigtail shape 30. For example, in another embodiment, the coil 52 may begin at an alternative coil starting point 62B located 180° from the start 57 of the pigtail shape 30. Alternatively, the coil 52 can begin at an alternative coil starting point 62C located 270° from the start 57 of the pigtail shape 30. In still other configurations, the coil 52 can begin at a location between about 180° to about 360°, about 180° to about 240°, or about 240° to about 300°, or about 300° to about 360° from the start 57 of the pigtail shape 30 based upon a desired location for the "weak point" or kink point.

Returning now to FIG. 2, the guidewire 28 may generally maintain a uniform outside diameter along the length of the guidewire 28. For example, the coil 52 may be placed over a distal portion 50 of the second section 46, however, due to tapering, the second section 46 may have an outside diameter equal to or less than the outside diameter of the first section 44. The tapering or narrowing of the elongated core 40 in the second section 46 may reduce the chance of puncturing the heart wall, while maintaining guidewire tip flexibility.

The guidewire 28 may include an atraumatic tip 54. The atraumatic tip 54 may comprise a distal portion 50 of the second section 46 of the guidewire 28. In some embodiments, the atraumatic tip 54 may comprise a pigtail shape 30 formed by a distal portion 50 of the second section 46 of the guidewire 28. In some embodiments, the atraumatic tip 54 may comprise the distal end 38. The atraumatic tip 54 may be a soft tip in order to avoid puncturing or damaging the left ventricle of the heart. Additionally, the pigtail shape 30 formed at the distal portion 50 of the second section 46 of the guidewire 28 may impart the guidewire 28 with the bending stiffness necessary to support the delivery catheter 24, as well as the ability to transition into an atraumatic soft tip which can be safely placed in the left ventricle during the procedure. Because of curved configuration associated with the pigtail shape 30, there is a decreased likelihood of damaging atrial and ventricle tissue when the guidewire 28 comes into contact with the tissue. For example, when the guidewire 28 contacts cardiac tissue 60 (FIG. 4), the curved orientation causes the guidewire 28 to roll or rotate in a direction of arrow A and decreases the force exerted on the atrial and ventricle tissue 60 by forming the pigtail shape 30. The guidewire 28 flexes and curves without penetrating the atrial and ventricle tissue 60. The pigtail shape 30 flexes and curves away from the atrial and ventricle tissue 60 resulting in the rolling motion of the guidewire 28. This rolling motion or rotary movement can be about an axis 61 of the pigtail shape 30, about the distal end 38 or atraumatic tip 54, or about some other axis.

The pigtail shape 30 may have a diameter of about 25 mm to 40 mm, 26 mm to 38 mm, 27 mm to 37 mm, 28 mm to 36 mm. In other embodiments the diameter of the pigtail shape 30 may be from about 5 mm to about 60 mm, from about 8 mm to about 55 mm, from about 10 mm to about 50 mm, from about 15 mm to about 45 mm, from about 20 mm to about 40 mm, or from about 20 mm to about 30 mm. The diameter of the pigtail shape 30 may be measured from the start 57 of the pigtail 30 and across to a bottom end 63 of the pigtail shape 30. The pigtail shape 30 may comprise a length of about 2% to 4% of the total length of a guidewire 28. In other embodiments the length may comprise about 3% to about 12% of the total length of a guidewire 28, about 3% to about 5% of the total length of a guidewire 28, about 4% to about 6% of the total length of a guidewire 28, about 5% to about 7% of the total length of a guidewire 28, about 6% to about 8% of the total length of a guidewire 28, about 7% to about 9% of the total length of a guidewire 28, or about 8% to about 10% of the total length of a guidewire 28.

The pigtail shape 30 may comprise a number of turns or rotations which may depend on the length of the guidewire, the desired size of the diameter of the pigtail shape 30, the size of the patient's heart, or any other factors which might cause a user to prefer a larger or smaller size pigtail shape

30. A pigtail shape 30 may comprise 1 to 10 turns. A turn may be defined as a 360° rotation of the distal end 38 of the guidewire 28 about the atraumatic tip 54, so that the distal end of the guidewire turns back on itself in progressively-sized concentric rings or spirals. For example, a small pigtail shape may include 1 to 3 turns. A medium pigtail shape may include 2 to 4 turns. A large pigtail shape may include 3 to 5 turns. An extra large pigtail shape may include 4-6 turns, and an extra large pigtail shape may include 7 to 10 turns. Dimensions within the foregoing ranges have been found to be effective in cardiac interventional procedures, particularly for guiding a delivery catheter or other catheter device in a mitral valve repair or replacement procedure.

Figure 6:
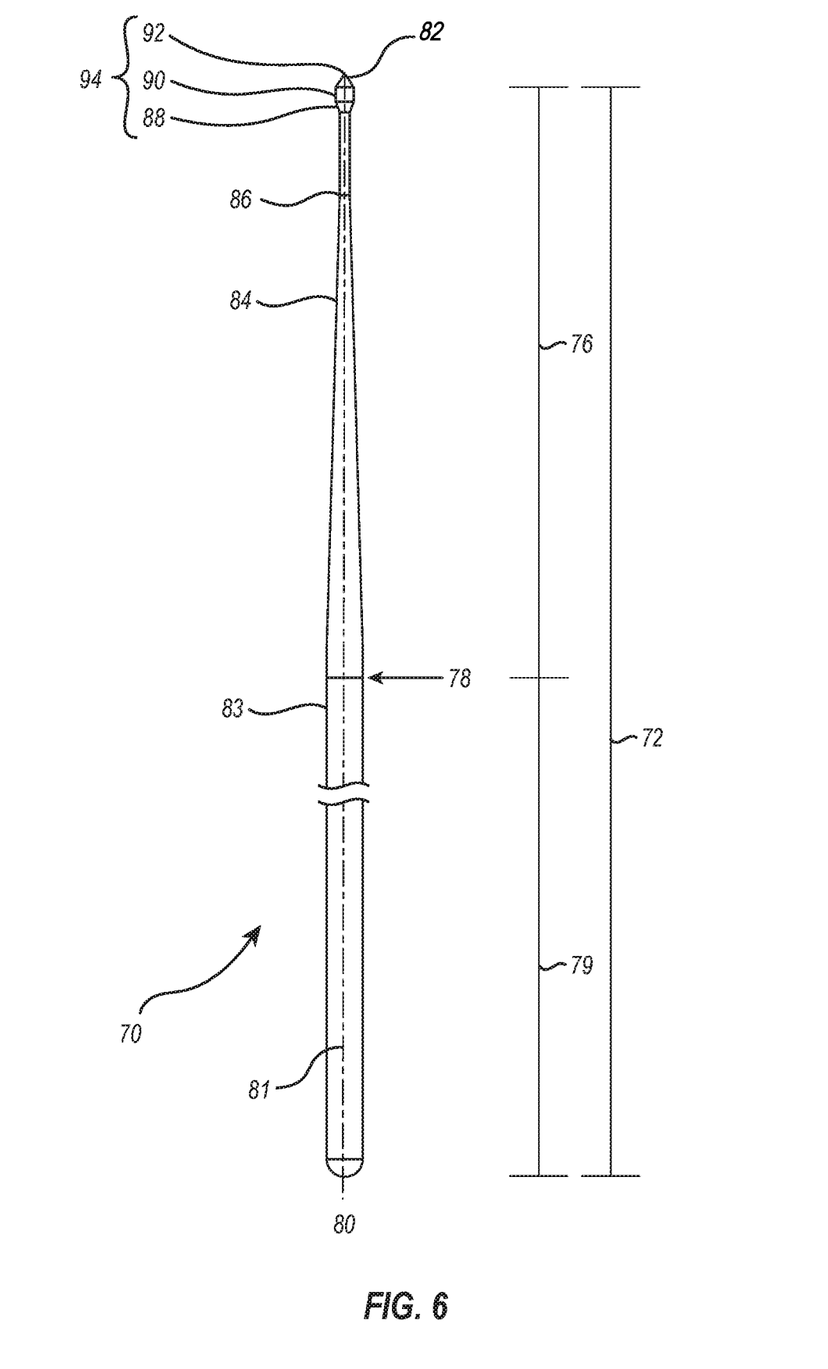
FIG. 6 discloses aspects of a side view of a guidewire according to one embodiment of the present disclosure.

In some embodiments, the guidewire may have multiple tapered sections and multiple sections with a generally uniform diameter. For example, as shown in FIG. 6, the guidewire 70 may have an elongate body 72 comprising a guidewire core 81 having a proximal end 80 and a distal end 82. The first section 79 of the guidewire 70 may have a generally uniform diameter. The first section 79 may comprise the proximal end 80 of the guidewire 70 and extend the length of the guidewire 70 towards the distal end 82 to a tapering point 78. In some embodiments, the length of the first section 79 may be about 5 mm to 15 mm long. In another embodiment the length of the first section 79 may be about 7 mm to 13 mm long. In another embodiment, the length of the first section 79 may be about 8 mm to 12 mm long. The tapering point 78 may define the end of the first section 79 of the guidewire 70 and the start of the second section 76 of the guidewire. The first section 79 may have a diameter of about 0.035 inches, for example, or any of the other guidewire diameters described above in relation to any other embodiment.

The second section 76 of the guidewire 70 may extend from the tapering point 78 through the distal end 82 of the length of the guidewire 70. In one embodiment, the second section 76 may comprise a first tapering section 84, a first uniform diameter portion 86 having a generally uniform diameter, a second tapering section 88, and a second uniform diameter section 90 having a generally uniform diameter. In some embodiments, the second tapering section 88 and the second uniform diameter section 90 may form the atraumatic tip 94. In some embodiments, the first tapering section 84 and the second tapering section 88 may taper in opposite directions. For example, as illustrated in FIG. 6, the first tapering section 84 tapers down or narrows as it approaches the distal end 82 of the guidewire 70, while the diameter of the second tapering section 88 increases towards the distal end 82. The second tapering section 88 may provide a transition between the coil 52 and the atraumatic tip 94, and may provide an effective location for attaching the distal end of the coil 52 to the core of the guidewire 70. In some embodiments, the atraumatic tip 94 may be formed from the second tapering section 88, the second uniform diameter section 90, and a rounded end portion 92 disposed on the distal end 82 or tip of the guidewire 70.

In one embodiment, the length of the first tapering section 84 may be about 180 mm to 200 mm long. In another embodiment, the length of the first tapering section 84 may be about 185 mm to 195 mm long. In another embodiment, the length of the first tapering section 84 may be about 187 mm to 193 mm long. In one embodiment, the combined length of the second tapering section 88 and second generally uniform section 90 may be about 2.5 mm to 4.5 mm long. In another embodiment, the combined length may be about 2.75 mm to 4.25 mm long. In another embodiment, the combined length may be about 3.0 mm to 4.0 mm long. Dimensions within the foregoing ranges have been found to be effective in cardiac interventional procedures, particularly for guiding a delivery catheter or other catheter device in a mitral valve repair or replacement procedure.

In one embodiment, the diameter of the second uniform section 90 may be about 0.170 mm to 0.210 mm. In another embodiment, the diameter of the second uniform section 90 may be about 0.175 mm to 0.205 mm. In another embodiment, the diameter of the second uniform section 90 may be about 0.180 mm to 0.200 mm.

Figure 7:
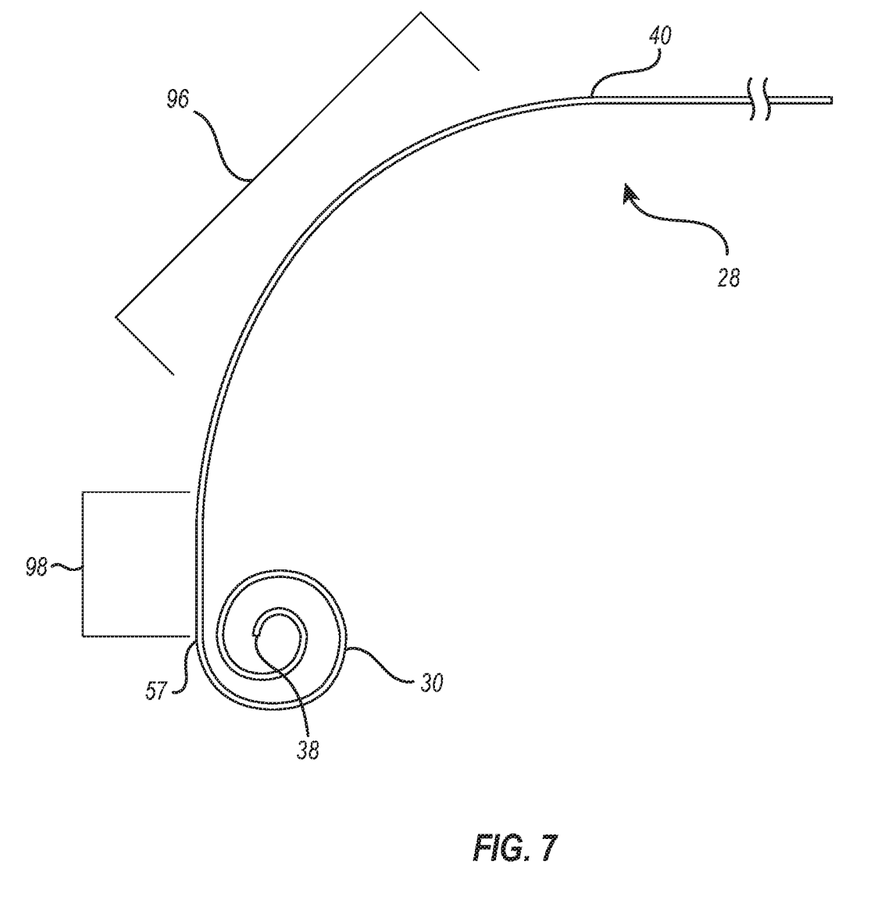
FIG. 7 discloses aspects of a side view of another guidewire according to one embodiment of the present disclosure.

Turning now to FIG. 7, in some embodiments, the guidewire 28 may include a pre-curved portion or a secondary bend 96 in the elongated core 40, proximal to the pigtail shape 30. In some embodiments, the secondary bend 96 of the elongated core 40 may comprise a section of the guidewire proximal to a straight length 98 of the guidewire, which is proximal to the start 57 of the pigtail shape 30. The straight length 98 may be a substantially straight line of zero curvature. The straight length 98 may provide additional support to the guidewire when the atraumatic tip or pigtail shape 30 is placed in the left ventricle. The secondary bend 96 of the elongated core 40 may allow the guidewire 28 to settle into the left atrium of the heart and provide a more secure rail for a delivery catheter 24 to track in order to deliver a valve prosthesis and/or other interventional device(s). The pre-curve portion 96 in the elongated core 40 may be advantageous as an elongated core 40 which has a pre-curve may be less likely to prolapse out of the left ventricle and into the left atrium. The pre-curve may also lessen the likelihood of the guidewire 28 becoming kinked by removing or lessening a potential weak point.

In the illustrated configuration, a radius of the pre-curved portion is about 4 cm. It will be understood, however, that the radius of the secondary bend 96 can be about 2 cm to 50 cm, about 4 cm to about 40 cm, 6 cm to about 30 cm, about 8 cm to about 20 cm.

Following are some further example embodiments of the invention. These are presented only by way of example and are not intended to limit the scope of the invention in any way.

Embodiment 1

A delivery guidewire, the delivery guidewire comprising: an elongated core with a proximal end, a distal end, and a length extending along a longitudinal axis therebetween, wherein the elongated core is made of a superelastic material. Optionally, a coil is also disposed on the elongated core and extends along the longitudinal axis of the elongated core, and an atraumatic tip disposed at the distal end of the elongated core, wherein the atraumatic tip comprises a pigtail shape.

Embodiment 2

A delivery guidewire as recited in Embodiment 1 wherein the elongated core comprises a first section having a generally uniform diameter and a second section comprising a tapered section.

Embodiment 3

A delivery guidewire as recited in any of Embodiments 1-2 wherein the first section is proximal to a second section and a tapering point defines the point at which the second section begins and the first section ends.

Embodiment 4

A delivery guidewire as recited in any of Embodiments 1-3, wherein the coil is disposed on a distal portion of the elongated core.

Embodiment 5

The delivery guidewire as recited in any of Embodiments 1-4, wherein an outer sleeve is disposed on the elongated core and extends from the proximal end to the distal end.

Embodiment 6

The delivery guidewire as recited in any of Embodiments 1-5, wherein the coil is disposed on a distal portion of the elongated core and extends along a length of the pigtail shape.

Embodiment 7

The delivery guidewire as recited in any of Embodiments 1-6, wherein the outer sleeve is a polymeric sleeve.

Embodiment 8

The delivery guidewire as recited in any of Embodiments 1-7, wherein the polymeric sleeve has a textured surface.

Embodiment 9

The delivery guidewire as recited in any of Embodiments 1-8, further comprising a secondary bend on the elongate core proximal to the atraumatic tip.

Embodiment 10

A delivery guidewire, the delivery guidewire comprising: an elongated core with a proximal end, a distal end, and a longitudinal axis therebetween. Wherein the elongated core comprises a first section of generally uniform diameter and a second section comprising a tapering section, wherein the first section is proximal to the second section, and wherein the first section is defined from the second section at a tapering point, and wherein the elongated core comprises a superelastic material. A coil disposed on the elongated core and extending along the longitudinal axis of the elongated core, and an atraumatic tip disposed at the distal end of the elongated core. Wherein the atraumatic tip is a pigtail shape formed by a distal portion of the second section of the elongated core.

Embodiment 11

The delivery guidewire as recited in Embodiment 10, wherein the elongated core has a straight length proximal to a start of the pigtail shape.

Embodiment 12

The delivery guidewire as recited in any of Embodiments 10-11, wherein the elongated core has a secondary bend proximal to the straight length.

Embodiment 13

The delivery guidewire as recited in any of Embodiments 10-12, wherein the pigtail shape has a curved orientation which causes the delivery guidewire to rotate and curve away from tissue.

Embodiment 14

The delivery guidewire as recited in any of Embodiments 10-13, wherein the coil is disposed on the distal portion of the second section of the elongated core.

Embodiment 15

The delivery guidewire as recited in any of Embodiments 10-14, wherein the coil extends along a length of the pigtail shape.

Embodiment 16

The delivery guidewire as recited in any of Embodiments 10-15, wherein the coil is a radiopaque coil.

Embodiment 17

The delivery guidewire as recited in any of Embodiments 10-16, wherein an outer sleeve is disposed on the elongated core and extends from the proximal end to the distal end.

Embodiment 18

The delivery guidewire as recited in any of Embodiments 10-17, wherein the tapering point is located about 0 cm to about 10 cm from a start of the pigtail shape.

Embodiment 19

A method of positioning the delivery guidewire as recited in any of Embodiments 1-18 to support a catheter in the heart, the method comprising: 1) advancing a first guidewire into a right atrium of a heart. 2) Puncturing a septum between the right atrium and a left atrium of the heart to form an opening. 3) Advancing the first guidewire into the left atrium through the opening in the septum. 4) Removing the first guidewire. 5) Exchanging the first guidewire for the delivery guidewire by advancing the distal end of the delivery guidewire into the right atrium, through the opening in the septum into the left atrium and through a mitral valve into a left ventricle of the heart. 6) Positioning the pigtail shape of the distal end of the delivery guidewire in the left ventricle of the heart, and 7) advancing a catheter along the delivery guidewire and into the heart.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that deviate by less than or equal to 5%, 1%, 0.1%, or 0.01% of a stated value.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A delivery guidewire, the delivery guidewire comprising:
 an elongated core with a proximal end, a distal end, and a length extending along a longitudinal axis therebetween,
  wherein the elongated core is made of a superelastic material;
 a coil disposed on the elongated core and extending along at least a portion of the length of the elongated core, the coil increasing a bending stiffness of a portion of the delivery guidewire; and
 an atraumatic tip disposed at the distal end of the elongated core,
  wherein the atraumatic tip comprises a pre-formed pigtail shape, the coil being disposed on the atraumatic tip and having a starting point distal a starting point of a first curved section of the pigtail shape formed in a distal portion of the elongate core, and a location of the starting point of the coil positions a location where a kink in the elongate core can form to within the pre-formed pigtail shape.

2. The delivery guidewire of claim 1, wherein the elongated core comprises a first section having a generally uniform diameter and a second section comprising a tapered section.

3. The delivery guidewire of claim 2, wherein the first section is proximal to a second section, and wherein a tapering point defines the point at which the second section begins and the first section ends.

4. The delivery guidewire of claim 1, wherein the coil is disposed on a distal portion of the elongated core.

5. The delivery guidewire of claim 1, wherein an outer sleeve is disposed on the elongated core and extends from the proximal end to the distal end.

6. The delivery guidewire of claim 5, wherein the outer sleeve is a polymeric sleeve.

7. The delivery guidewire of claim 6, wherein the polymeric sleeve has a textured surface.

8. The delivery guidewire of claim 1, wherein the coil is disposed on a distal portion of the elongated core and extends along a length of the pigtail shape.

9. The delivery guidewire of claim 1, further comprising a secondary bend on the elongate core proximal to the atraumatic tip.

10. A delivery guidewire, the delivery guidewire comprising:
 an elongated core with a proximal end, a distal end, and a length extending along longitudinal axis therebetween,
  wherein the elongated core comprises a first section of generally uniform diameter and a second section comprising a tapering section, wherein the first section is proximal to the second section, and wherein the first section is defined from the second section at a tapering point, and
  wherein the elongated core comprises a superelastic material; and
 an atraumatic tip disposed at the distal end of the elongated core,
  wherein the atraumatic tip is a pigtail shape formed by a distal portion of the second section of the elongated core, a coil being disposed on the atraumatic tip and having a starting point distal a starting point of a first curved section of the pigtail shape formed in a distal portion of the elongate core, the coil increasing a bending stiffness of a portion of the second section and a location of the starting point of the coil positions a location where a kink in the elongate core can form to within the pigtail shape.

11. The delivery guidewire of claim 10, further comprising the coil disposed on the elongated core and extending along at least a portion of the elongated core.

12. The delivery guidewire of claim 11, wherein the coil is disposed on the distal portion of the second section of the elongated core.

13. The delivery guidewire of claim 11, wherein the coil extends along a length of the pigtail shape.

14. The delivery guidewire of claim 11, wherein the coil is a radiopaque coil.

15. The delivery guidewire of claim 10, wherein the elongated core has a straight length proximal to a start of the pigtail shape.

16. The delivery guidewire of claim 15, wherein the elongated core has a secondary bend proximal to the straight length.

17. The delivery guidewire of claim 10, wherein the pigtail shape has a curved orientation which causes the delivery guidewire to rotate and curve away from tissue.

18. The delivery guidewire of claim 10, wherein an outer sleeve is disposed on the elongated core and extends from the proximal end to the distal end.

19. The delivery guidewire of claim 10, wherein the tapering point is located about 0 cm to about 10 cm from a start of the pigtail shape.

20. A method of positioning the delivery guidewire of claim 1 to support a catheter in the heart, the method comprising:
 advancing a first guidewire into a right atrium of a heart;
 puncturing a septum between the right atrium and a left atrium of the heart to form an opening;
 advancing the first guidewire into the left atrium through the opening in the septum;
 removing the first guidewire;
 exchanging the first guidewire for the delivery guidewire by advancing the distal end of the delivery guidewire into the right atrium, through the opening in the septum into the left atrium and through a mitral valve into a left ventricle of the heart;
 positioning the pigtail shape of the distal end of the delivery guidewire in the left ventricle of the heart; and
 advancing a catheter along the delivery guidewire and into the heart.

* * * * *